United States Patent [19]

Shafer

[11] Patent Number: 4,812,241
[45] Date of Patent: Mar. 14, 1989

[54] SAMPLE TRANSFER FOR INFRARED ANALYSIS IN THIN LAYER CHROMATOGRAPHY-STRUCTURE & METHOD

[75] Inventor: Kenneth H. Shafer, Costa Mesa, Calif.

[73] Assignee: Laser Precision Corporation, Irvine, Calif.

[21] Appl. No.: 197,702

[22] Filed: May 23, 1988

Related U.S. Application Data

[63] Continuation-in-part of Ser. No. 85,403, Aug. 14, 1987, abandoned.

[51] Int. Cl.$^4$ .............................................. B01D 15/08
[52] U.S. Cl. .................................. 210/658; 210/198.3; 73/61.1 C; 422/66; 422/70; 436/44; 436/162; 436/167
[58] Field of Search ..................... 210/635, 658, 198.3; 73/61.1 C; 422/66, 68, 70, 90; 436/44, 46, 162, 167

[56] References Cited

U.S. PATENT DOCUMENTS

| | | | |
|---|---|---|---|
| 3,864,263 | 2/1975 | Jethwa | 210/198.3 |
| 3,928,203 | 12/1975 | Kremer | 210/198.3 |
| 4,004,548 | 1/1977 | Smola | 210/198.3 |
| 4,228,008 | 10/1980 | Karol | 210/198.3 |
| 4,272,381 | 6/1981 | Kremer | 210/198.3 |
| 4,696,187 | 9/1987 | Kopp | 436/162 |

FOREIGN PATENT DOCUMENTS 2646640 4/1978 Fed. Rep. of Germany ... 210/198.3

OTHER PUBLICATIONS

Shafer, Sample Transfer Accessory for Thin Layer Chromatography Fourier Transform Infrared Spectrometer, Anal. Chem., Nov. 1986, 58, pp. 2708-2714.

Primary Examiner—Ernest G. Therkorn
Attorney, Agent, or Firm—Thomas J. Plante

[57] ABSTRACT

A chromatography sample transfer process is disclosed in which fractions on a TLC plate are automatically moved by capillary action from the plate to separate receptacles adapted to retain material for diffuse reflectance measurement. The developed TLC plate is so mounted that its fractions are horizontally spaced, and its lower edge is in a solvent. As the solvent moves upwardly due to capillarity, it dissolves the fraction samples, and transfers them to a plurality of horizontally spaced wicks. The wicks, which are preferably made of sintered stainless steel powder, carry their solvent/sample material upwardly to separate receptacles, each containing transparent powder which retains the sample during diffuse reflectance measurement. The solvent is removed from the receptacles by horizontal airflow (air knife) without requiring significant heating.

29 Claims, 3 Drawing Sheets

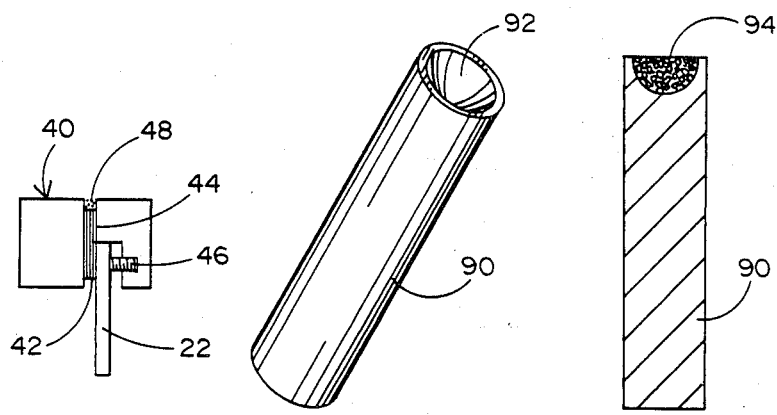
FIG. 6　　FIG. 10　　FIG. 11
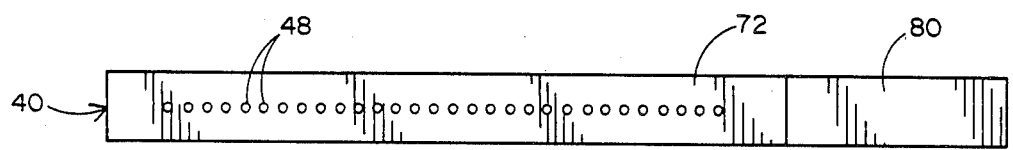
FIG. 7
FIG. 8
FIG. 9

SAMPLE TRANSFER FOR INFRARED ANALYSIS IN THIN LAYER CHROMATOGRAPHY-STRUCTURE & METHOD

This application is a continuation-in-part of application Ser. No. 085,403, filed Aug. 14, 1987, now abandoned.

BACKGROUND OF THE INVENTION

This invention relates to the use of Fourier Transform infrared (FTIR) spectroscopy in the analysis of thin layer chromatography (TLC) samples.

The use of the diffuse reflectance mode of FTIR spectroscopy has greatly improved the effectiveness of TLC techniques. Prior to the combination of FTIR and TLC techniques, the use of TLC had lagged behind the use of high performance liquid chromatography (HPLC).

Until recently, the general use of a combined TLC/FTIR system in the analysis of samples was very clumsy and time-consuming. After the separated samples were deposited on a TLC plate, each sample was scraped off the plate (usually a silica-gel-precoated plate) and then transferred to a receptacle, such as a cup containing powdered potassium bromide (KBr), where it was submitted to diffuse reflectance FTIR spectroscopy.

The problem of sample transfer has been a deterrent in the use of TLC/FTIR. The samples cannot be successfully analyzed without removal from the TLC plate, because the silica powder on the plate is both chemically active and radiation absorbing.

A significant advance in this field, involving automatic sample transfer, was discussed in an article titled "Sample Transfer Accessory for Thin-Layer Chromatography/Fourier Transform Infrared Spectrometry" by Shafer, Griffiths and Shu-Qin, which appeared in "Analytic Chemistry, 1986, 58, pages 2708-2714. The article described a "sample transfer approach to thin-layer chromatography/Fourier transform infrared spectrometry (TCL/FT-IR) * * in which each separated component is moved simultaneously from the TLC plate to an IR-transparent substrate prior to measurement of its diffuse reflectance spectrum." As stated in the article, "more spectral information is obtained about the analytes and in significantly less time than is required for in situ measurements. The transfer is accomplished with minimal sample loss, decomposition, or contamination compared with previous processes."

In the prior art arrangement, the developed TLC plate was turned 90° and placed in solvent contained in a reservoir. Using a multiplicity of vertically-extending wicks, the horizontally spaced samples were moved upwardly by the solvent and the wicks into a row of cups each containing a diffuse reflectance powder, such as a "finely-ground infrared-transmitting glass (powder) composed of germanium, antimony and selenium".

The transfer process described above is highly desirable as a TLC/FTIR sub-process. However, significant problems have been encountered in attempting to use this transfer process. Various forms of wicks have proved unsuccessful, particularly because of swelling problems, which, of course, interfere with the desired capillary upward motion of the dissolved samples. Also, imperfect sample drying at the powder-containing cups has been a particularly difficult problem to solve. If drying occurs too quickly, the full sample will not reach the diffuse reflectance cups. If drying occurs too slowly, part of the sample will be carried out above the cups by the solvent. The heating step mentioned in the cited article as a means of solvent removal has not proved to be desirable as a drying method. Yet another problem in the prior art arrangement was the tendency to cause substantial contamination due to excessive handling of elements which contacted the transfer solvent.

SUMMARY OF THE PRESENT INVENTION

In general, the present invention has provided an efficiently working sample transfer process and apparatus for a TLC/FTIR system. It incorporates vertical wicks and laterally spaced powder cups, as in the disclosure discussed above.

However, the solvent removal (drying) problem at the cups has been effectively solved by using a non-heated uniform airflow, i.e., an "air knife", which can provide rapid, low pressure horizontal flow of air across the tops of the cups.

The solution to the problem of wick failures has been the use of sintered metal wicks, using a powdered metal which is chemically inert, e.g., stainless steel. These wicks have the necessary capillary effect because of their porosity.

The combination of the air knife and the sintered metal wicks has successfully resolved the problems involved in (a) getting the samples to the diffuse reflectance material in the cups; and (b) keeping the combined samples and reflectance materials in position for reflectance analysis.

The structures of the present invention also are particularly compatible with automatic feeding devices, which move a row of separated fraction samples seriatim into position for illumination in a diffuse reflectance spectrometer accessory.

Additionally, the present invention minimizes the contamination problems due to handling of transfer-system elements. Those elements are combined in a subassembly which is inserted from the top of the transfer chamber.

In one version of the invention, the powder-holding cups are formed integrally with the sintered metal wicks.

BRIEF DESCRIPTION OF THE DRAWINGS

FIG. 1 shows schematically a conventional TLC separation unit; FIG. 2 shows a strip along which wicks and diffuse reflectance cups are mounted; and FIG. 3 shows a complete sample transfer unit.

FIG. 6 is a closeup of the wick and diffuse reflectance cup of FIG. 4;

FIGS. 7, 8 and 9 are top, side, and bottom views, respectively, of the "optitrain", a long metal sub-assembly which supports the wicks and samples during the TLC transfer process, and during the subsequent diffuse reflectance analysis; and FIGS. 10 and 11 show enlarged views of another embodiment of the sintered metal wicks, in which their upper ends provide cup-shaped recesses for retention of the powdered matrix material.

DETAILED DESCRIPTION OF THE SPECIFIC EMBODIMENT

Figure 1:
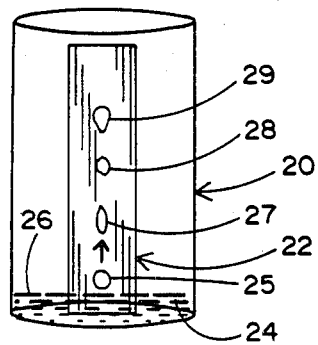
FIGS. 1-3 are isometric views showing a TLC/FTIR sample transfer system initially used by the assignee of the present application.

FIG. 1 shows a conventional TLC separation unit. A tank 20 contains a vertically extending TLC plate (chromatoplate) 22, the lower edge of which extends into a solvent 24. The original sample 25 is deposited on plate 22, just above the solvent line 26. The plate 22 has a coating (stationary phase) which encourages capillary action, i.e., movement of the solvent upwardly along the side of the plate as a result of capillarity. This is the well-known action in which the surface of a liquid, where it contacts a solid, is elevated or depressed, because of the relative attraction of the molecules of the liquid for each other and for those of the solid.

The separation of constituents of the sample into fractions is the basis of chromatography. In FIG. 1, the separated fractions are illustrated by vertically spaced spots 27, 28 and 29 (replacing initial spot 25). The different locations of the separated fractions result from their chemical responses to the moving and stationary phases, i.e., the constituents of the initial sample separate out at different rates, and thus reach different vertical levels on plate 22.

The coating for TLC plate 22 is usually a silica gel, a powder which is important in the fraction separation process. The qualities which make the material very useful during the fraction separation process, make it very inappropriate as a base during optical analysis by a diffuse reflectance accessory. As stated above, the powdered coating on TLC plate 22 would absorb, rather than reflect, the analytical radiation.

It is, therefore, necessary to transfer the separated samples (27, 28 and 29) on TLC plate 22 to a favorable matrix for diffuse reflectance analysis. In the past, this has often been done by scraping the material in each such sample off the plate, mixing it with a suitable matrix material, and then inserting the mixture into a receptacle.

Figure 2:
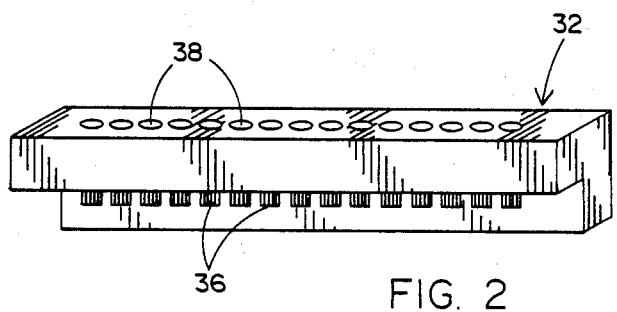
Figure 3:
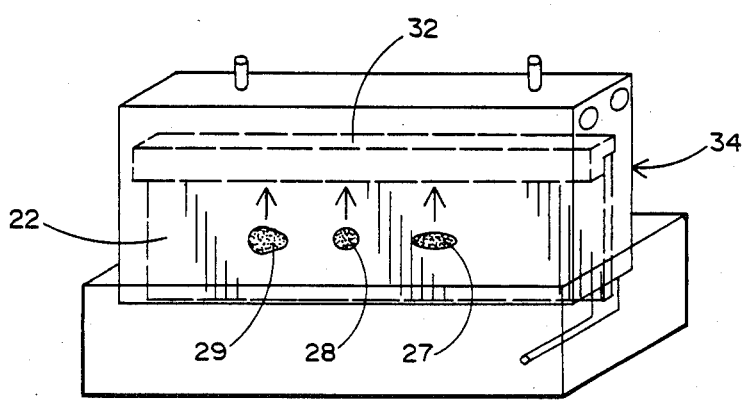

In FIGS. 2 and 3, an automatic transfer system is shown. A fraction-receiving metal strip 32 is shown inserted in a sealed solvent chamber 34. Also inserted into the chamber 34, below strip 32, is the TLC plate 22, which has been turned 90° from its position in tank 20 of FIG. 1. Thus, the separated fractions 27, 28 and 29 are horizontally, rather than vertically, spaced from one another. Solvent is introduced into chamber 34, to a level which reaches the lower, horizontally-extending, edge of TLC plate 22. The metal strip 32 and TLC plate 22 are a preassembled unit, which is inserted from the top of chamber 34, in order to minimize contamination, as discussed below in greater detail.

The solvent in chamber 34 is drawn upwardly by capillary action across the TLC plate. As it passes over the separated fractions 27–29, it dissolves them, and carries them upwardly by continued capillary movement. The fractions do not recombine, because of their horizontal spacing.

Continued upward capillary motion brings the separated fractions to individual, vertically-extending, horizontally-spaced, wicks 36, each of which leads to a separate cup, or receptacle, 38 (containing diffuse reflectance powder) in the top of strip 32. There are a multiplicity of such wick/cup combinations. It is important that there be enough separate wick-cup combinations to prevent recombination of the separated fractions. An additional method of preventing recombination is the forming of boundaries by cutting vertical channels. In determining the preferred number of wicks, a trade-off must be resolved in order to have a number large enough to avoid recombination, but not so large as to reduce sample concentration, and thus cause loss of signal intensity at the diffuse reflectance cups 38.

Figure 4:
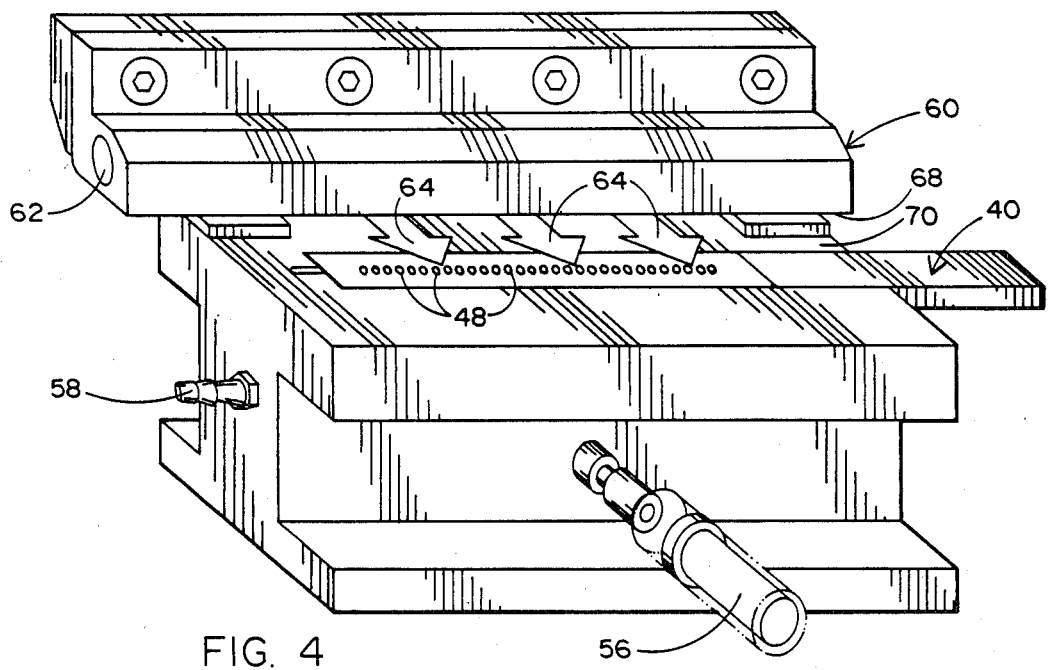
FIG. 4 is an isometric view of the TLC transfer apparatus of FIGS. 5 and 6.
Figure 5:
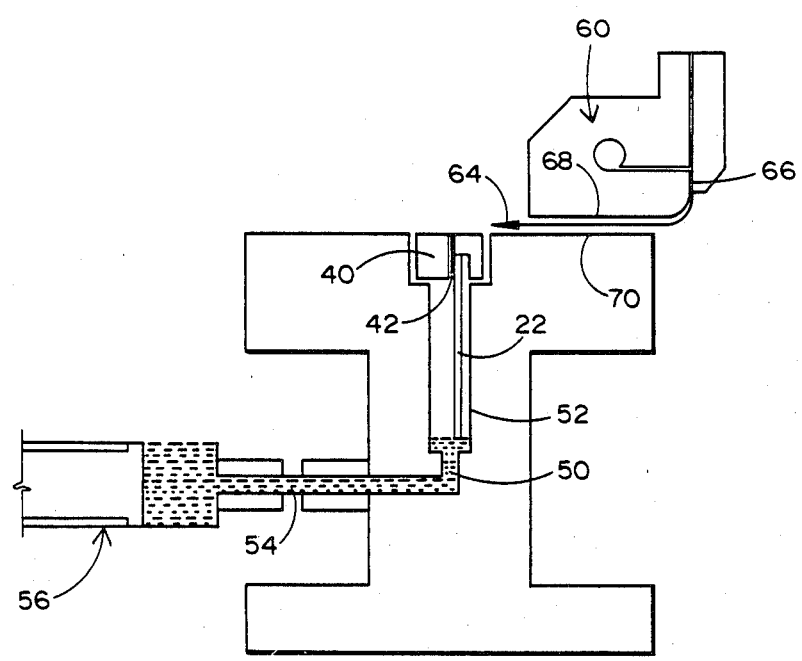
FIG. 5 is a schematic showing from one side the preferred TLC transfer apparatus of the present invention.

FIGS. 4, 5 and 6 show a TLC transfer system incorporating the vital improvements provided by the present invention. FIG. 6 shows the relative positioning of the wicks, reflectance cups, their carrier strip, and the TLC plate. The carrier strip 40, called an "optitrain", is shown in cross-section. Each of a plurality of wicks 42 is pressed against one wall of its bore 44 by engagement with TLC plate 22, which is held in place by a plurality of set screws 46 threaded into the body of strip 40. Supported in a cup 48 on top of each wick 42 is an infrared transparent powder which retains the separated fraction during diffuse reflectance measurement. The powdered material is a suitable glass-like material which has been packed into its cup-shaped opening. (Although FIGS. 5 and 6 do not differentiate the bore diameters which contain each wick 42 and its contiguous reflectance powder 48, in the preferred embodiment of the invention, the diameter of the powder-containing cup is substantially less than that of the wick).

The parts shown in FIG. 6 constitute a subassembly which is inserted as a unit into the top of the structure shown in FIG. 5. This subassembly, which is handled by the operator, does not contact the solvent except at its bottom edge; and therefore is not a cause of solvent contamination.

FIG. 5 shows the solvent/fraction flow path. Solvent 50 is admitted to a chamber 52 through a passage 54, and is injected by a syringe 56 which provides controlled delivery (and evacuation) of the solvent. It is important that the solvent 50 contact uniformly the lower edge of TLC plate 22. It is also important to minimize the volume of chamber 52, so that a minimum of solvent is evaporated before equilibration is obtained between the liquid and gas states. To prevent injection of too much solvent, a controlled overflow path 58 (FIG. 6) is provided.

The capillary action of the fraction-carrying solvent moves it from TLC plate 22 onto the individual wicks 42, and thence to the individual diffuse reflectance cups 48. At this point, it is important to remove the solvent, while retaining as much as possible of the sample material (fraction) in each cup 48. The problems are twofold. On one hand, if the solvent is evaporated too quickly, the samples will not reach the cups 48 in sufficient quantity, i.e., they will remain, at least partially, on the wicks. On the other hand, if the solvent is evaporated too slowly, it will carry some of the sample material out of the cups, thus losing it for subsequent spectroscopic analysis.

Extensive efforts to obtain satisfactory performance of an automatic TLC transfer system have led to the conclusions (a) that the use of the optimum wick material is vital; and (b) that the solvent-removing method is vital.

Before fully explaining these features, attention is called to the airflow method of removing the solvent, which is illustrated in FIGS. 4 and 6. A device referred to as an "air knife" is shown at 60. This device relies on the coanda effect, i.e., wall attachment of a high velocity fluid. The air knife 60 is a product of the Exxair Corporation. It has two opposite end inlets 62 for compressed air, and has internal air distribution channels which result in horizontally-directed airflow, indicated by arrows 64, which flow is evenly distributed across the horizontal upper surface of optitrain 40, and thus across the tops of the reflectance powder cups 48. The restriction in the flow of compressed air from the air knife 60 is the very thin (0.002 to 0.003 inch) slot 66. Because of the coanda effect, the air forced through slot 66 travels along the undersurface 68 of the air knife device, passing between that surface and the top surface 70 of the housing which contains chamber 52 and supports optitrain 40.

The flow of air from air knife device 60 is augmented by air drawn into the space between surfaces 68 and 70. By regulating the velocity of airflow upstream of the air knife, it is possible to provide a controlled airflow rate across the optitrain which will cause surface evaporation of the solvent, while it causes the fraction samples to reach, and remain in, their diffuse reflectance powder cups 48. The best results occur when the airflow is in the range of 20 to 50 cubic feet per hour. This velocity should be so adjusted that the airflow is horizontal, i.e., has substantially a zero angle of incidence on the sample-holding powdered material. The airflow should not drive the sample-carrying solvent down toward the wicks 42; nor should it permit evaporation delay which would cause sample material to exit from the tops of the cups 48.

An important advantage of the airflow evaporation device is that it reduces or eliminates the need for heating the optitrain to cause evaporation. Heating hss sometimes proved undesirable, because it tends to prematurely evaporate the solvent, causing the sample material to clog the wicks 42, and not reach the cups 48.

As stated above, a number of experimental efforts to provide automatic fraction transfer have failed because of the characteristics of the wicks. In the Shafer et al article cited above, the suggested wick material was glass fibers. Those wicks did not prove satisfactory, because of poor capillarity, poor contact, and lack of durability. Subsequently, polymer wicks were tested extensively. However, they failed to function properly. They had a tendency to expand and contract, thus inhibiting smooth solvent capillary flow. Also, they were susceptible to chemical reactions with the materials being transferred.

It appears that the best material for forming the wicks 42 is an inert powdered metal, which has been sintered, i.e., fused under heat and pressure. Stainless steel is considered the preferred metal. It is chemically inert; its sintered form has good capillary action; and it does not vary in dimensions (i.e., expand or contract in this usage). Metals such as aluminum and brass are not desirable because they are not chemically inert.

It is clear that the effective functioning of the wicks is a sine qua non of a TLC transfer system. The proper functioning of the optitrain depends in part on wicks being inert and insoluble in solvents used for fraction transport, maintaining constant size and shape (i.e., not shrinking or expanding) while in contact with solvents. The variance in diameter of each wick must be minimal so as to maintain uniform contact with the TLC plate stationary phase. Variance in length of each wick must be minimal so as to maintain uniform contact with the IR powder located at the top of the optitrain. And the diameter of each wick needs to be small enough to allow or an appropriate number of wicks per spot diameter (i.e., maintain chromatographic resolution during transfer). The wicks need to be easily replaced by the user in instances where wicks are damaged due to excessive contamination. Instead of the wicks being placed in every hole of the optitrain, only those positions in the optitrain which are opposite spots on the chromatoplate may be used. In this instance, each spot is confined to a single cup during transfer, resulting in increased sensitivity. In order to perform this task, the wicks need to be easily removed and inserted.

FIGS. 7-9 show details of the construction of optitrain 40. It is used both in the sample transfer structure of this application, and in a subsequently used automated diffuse reflectance spectroscope accessory. It conveniently has two metal strips secured together, an upper strip 72, and a lower strip 74. The upper strip 72 has a series of small recesses 76 formed by boring through the strip 72, and a series of aligned larger recesses 78 formed by counterboring from the bottom of the strip. The wicks 42 are inserted from the bottom of strip 72 into recesses 78; and they engage the rims formed between recesses 76 and recesses 78. The wicks do not have a tight fit in recesses 78, because maximum capillary action is desired. The powdered IR transparent material 48 is packed into recesses 76, and engages the tops of the respective wicks 42; so that capillary action continues to move the solvent (and its sample material) into the recesses (receptacles, cups) 76. The diameters of cups 76 are smaller than the wick diameters, in order to provide an increase in reflectance sensitivity due to concentration.

The primary functions of the lower metal strip 74 are to support the lower edges of the wicks, and to provide a convenient handle 80 by which the optitrain is moved manually. The strip 74 has a longitudinal slot 82 through which the TLC plate 22 extends. At one side of slot 82, a ledge 84 extends just far enough to provide support for the bottom ends of the wicks, without interfering significantly with their capillary effect.

The air knife effectively evaporates the solvent from cups 48/76, leaving behind the sample concentrated at the surface of the IR powder. This is usually accomplished without heating the sample. The capability of concentrating the sample in the top portion of the powder is important in the success of the technique. In addition, the need for a minimum of heating, or in most instances no heating, means that thermally labile compounds can be analyzed. This is very important, as gas chromatography, a competitive separation technique, cannot be used for such samples. Because the solvent is evaporated automatically at the surface of the powder, the transfer does not have to be monitored by the user. The transfer is thus automated by the ability to control the evaporation of the solvent during transfer. During transfer, each spot may arrive at the top of the optitrain at different times. In most cases, the arrival of the spot will be difficult to determine, as most compounds will not be visible. It is important to the success of the technique that the arrival of each spot at the surface of the powder does not have to be determined by the user. The controlled evaporation of solvent is thus a very important fundamental task of the TLC transfer system.

It appears that certain advantages may be obtained by forming the sintered metal wicks in such a way that each provides a cup-shaped (hemi-spherical) recess into which is packed the powdered matrix material which retains the sample during diffuse reflectance measurement.

In FIG. 10, a wick 90 is shown, in the top of which a cup-shaped recess 92 has been formed during the sintering process. The dimensions of each wick 90 may be, as an example, 0.25 in. long, and 0.050 in. in diameter. FIG. 11 is a section through wick 90 taken on a vertical plane. Powdered glass material 94 has been packed into the recess in the top of the wick. The use of wicks of the type shown in FIGS. 10 and 11 will probably require a redesign of the optitrain element 40, because the tops of the wicks preferably will extend closer to the top of the optitrain. The wicks 90 could be inserted into openings in the optitrain from the top, but they need to be held in place if the optitrain is accidentally turned upside down.

There are several potential advantages in using the integrated wick/cup structure of FIGS. 10 and 11. One is the assurance of engagement of the powdered glass with the wick, avoiding any problems of discontinuity in the sample path. Also, since the wick material provides greater capillary action than the powder, distribution of the sample into the powder should be more efficient.

Another benefit is the capability of pre-packing the glass powder, which packs well in the wick, before the structure is supplied to the user. And the individual wicks may be easily removed from the optitrain, and replaced, if they become defective, or if cleaning is needed. In other words, the entire optitrain need not be handled because of a few contaminated samples.

From the foregoing description, it will be apparent that the apparatus and method disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A sample transfer system for moving fractions from a thin layer chromatography plate to a diffuse reflectance spectrometer accessory, comprising:
   a chamber in which the transfer occurs;
   a thin layer chromatography plate in the chamber, so located that its separated fractions are spaced horizontally from one another;
   an amount of solvent in the chamber into which the lower edge of the plate extends;
   a plurality of horizontally-spaced wicks engaging the upper edge of the plate, each of said wicks being formed of fused powdered metal which is essentially chemically inert;
   a plurality of horizontally-spaced receptacles each engaging the upper end of one of the wicks, and each containing powdered material which is transparent to analytical radiation;
   the arrangement being such that capillary action moves solvent upwardly to dissolve material in a separated fraction on the plate, and then carry it upwardly through a wick to a receptacle; and
   an airflow means for evaporating the solvent while retaining the material of the separated fraction in its receptacle.

2. The sample transfer system of claim 1 which also comprises a fraction-receiving strip which:
   has formed therein the horizontally-spaced receptacles;
   includes a handle for inserting and removing it from the top of the transfer chamber; and
   is adapted to be inserted into a diffuse reflectance accessory, and to be moved from station to station therein for individual analyses of the material of each receptacle.

3. The sample transfer system of claim 1 in which the material composing the sintered metal wicks is stainless steel.

4. The sample transfer system of claim 1 which also comprises:
   means for adjusting the airflow rate to maximize the arrival of fraction material at the receptacles and minimize the escape of such material from the receptacles.

5. The sample transfer system of claim 1 which also comprises:
   a longitudinally extending strip which carries the wicks and provides the receptacles.

6. The sample transfer system of claim 5 in which the chromatography plate and the strip are secured together in a subassembly which is inserted into the top of the chamber.

7. The sample transfer system of claim 5 in which the strip comprises:
   a first metal layer having larger holes extending into its bottom surface to receive the upper ends of the wicks, and smaller holes extending into its upper surface aligned, respectively, with the larger holes, and adapted to provide the receptacles; and
   a second metal layer secured to the bottom of the first layer, and having means for preventing displacement of the wicks.

8. The sample transfer system of claim 7 in which the wicks have minimum lateral engagement with adjacent surfaces, in order to permit maximum capillary action.

9. The sample transfer system of claim 1 wherein the angle of incidence of the airflow on the tops of the receptacles is essentially zero.

10. A method of transferring fractions from a thin layer chromatography plate to a diffuse reflectance spectrometer accessory, comprising:
    providing a chamber-containing housing for use in the transfer process;
    supplying solvent material to the lower portion of the chamber;
    inserting a TLC plate in the chamber, so positioned that its separated fractions are horizontally spaced from one another, and that capillary action moves the solvent vertically from the lower to the upper edge of the plate, during which movement the fractions are dissolved in the solvent;
    providing a plurality of vertically-extending, horizontally-spaced sintered steel wicks which move the fraction-carrying solvent upwardly by capillary action;
    transferring the fraction-carrying solvent from each wick to a separate receptacle containing powdered transparent material; and
    removing the solvent, but not the fraction material, from the receptacles by means of a substantially unheated, high flow rate, airflow which moves essentially in a horizontal plane across the top of the housing.

11. The method of claim 10 in which:
    the wicks are retained and the receptacles are provided, in a unitary strip.

12. The method of claim 11 in which:
    the TLC plate and unitary strip are combined in a subassembly; and the subassembly is inserted into the top of the chamber prior to supplying the solvent material.

13. The method of claim 10 in which:
individual wicks are readily removed and/or replaced between separate transfer operations.

14. The method of claim 10 in which:
the airflow rate is adjusted to maximize the arrival of fraction material at the receptacles and minimize the escape of such material from the receptacles.

15. A sample transfer system for moving fractions from a thin layer chromatography plate to a diffuse reflectance spectrometer accessory, comprising:
a chamber in which the transfer occurs;
a thin layer chromatography plate in the chamber, so located that its separated fractions are spaced horizontally from one another;
an amount of solvent in the chamber into which the lower edge of the plate extends;
a plurality of horizontally-spaced wicks engaging the upper edge of the plate, each of said wicks being formed of fused powdered metal which is essentially chemically inert; and
a plurality of horizontally-spaced receptacles each located at the upper end of one of the wicks, and each containing powdered material which is transparent to analytical radiation;
the arrangement being such that capillary action moves solvent upwardly to dissolve material in a separated fraction on the plate, and then carry it upwardly through a wick to a receptacle.

16. The sample transfer system of claim 15 in which each receptacle for powdered material is formed as a recess in the upper end of its fused powdered metal wick.

17. The sample transfer system of claim 15 which also comprises:
a multiple fraction holding strip which has formed therein a plurality of horizontally spaced openings, each of which exposes a sample-containing receptacle to the diffuse reflectance spectrometer accessory.

18. The sample transfer system of claim 17 in which the chromatography plate and the strip are secured together in a subassembly which is inserted into the top of the chamber.

19. The sample transfer system of claim 15 in which the material composing the sintered metal wicks is stainless steel.

20. A sample transfer system for moving fractions from a thin layer chromatography plate to a diffuse reflectance spectrometer accessory, comprising:
a chamber in which the transfer occurs;
a thin layer chromatography plate in the chamber, so located that its separated fractions are spaced horizontally from one another;
an amount of solvent in the chamber into which the lower edge of the plate extends;
a plurality of horizontally-spaced wicks engaging the upper edge of the plate;
a plurality of horizontally-spaced receptacles each located at the upper end of one of the wicks, and each containing powdered material which is transparent to analytical radiation;
the arrangement being such that capillary action moves solvent upwardly to dissolve material in a separated fraction on the plate, and then carry it upwardly through a wick to a receptacle; and
an airflow means for evaporating the solvent while retaining the material of the separated fraction in its receptacle.

21. The sample transfer system of claim 20 which also comprises:
means for adjusting the airflow rate to maximize the arrival of fraction material at the receptacles and minimize the escape of such material from the receptacles.

22. The sample transfer system of claim 20 wherein the angle of incidence of the airflow on the tops of the receptacles is essentially zero.

23. A method of transferring fractions from a thin layer chromatography plate to a diffuse reflectance spectrometer accessory, comprising:
providing a chamber-containing housing for use in the transfer process;
supplying solvent material to the lower portion of the chamber;
inserting a TLC plate in the chamber, so positioned that its separated fractions are horizontally spaced from one another, and that capillary action moves the solvent vertically from the lower to the upper edge of the plate, during which movement the fractions are dissolved in the solvent;
providing a plurality of vertically-extending, horizontally-spaced, wicks which move the fraction-carrying solvent upwardly by capillary action;
transferring the fraction-carrying solvent from each wick to a receptacle containing powdered transparent material; and
removing the solvent, but not the fraction material, from the receptacles by means of a substantially unheated, high flow rate, airflow which moves essentially in a horizontal plane across the top of the housing.

24. The method of claim 23 in which:
the airflow rate is adjusted to maximize the arrival of fraction material at the receptacles and minimize the escape of such material from the receptacles.

25. A method of transferring fractions from a thin layer chromatography plate to a diffuse reflectance spectrometer accessory, comprising:
providing a chamber-containing housing for use in the transfer process;
supplying solvent material to the lower portion of the chamber;
inserting a TLC plate in the chamber, so positioned that its separated fractions are horizontally spaced from one another, and that capillary action moves the solvent vertically from the lower to the upper edge of the plate, during which movement the fractions are dissolved in the solvent;
providing a plurality of vertically-extending, horizontally-spaced sintered metal wicks which move the fraction-carrying solvent upwardly by capillary action;
transferring the fraction-carrying solvent from each wick to a receptacle containing powdered transparent material; and
removing the solvent, but not the fraction material, from the receptacles.

26. The method of claim 25 in which:
the wicks and the receptacles are supported by a unitary strip.

27. The method of claim 26 in which:
the TLC plate and unitary strip are combined in a subassembly; and the subassembly is inserted into the top of the chamber prior to supplying the solvent material.

28. The method of claim 25 in which:

individual wicks are readily removed and/or replaced between separate transfer operations.

29. The method of claim 25 in which the sintered metal wicks are so formed as to provide a recess for holding the powdered transparent material.

* * * * *